United States Patent [19]
Allard et al.

[11] Patent Number: 5,525,359
[45] Date of Patent: Jun. 11, 1996

[54] MICROCAPSULES HAVING A COMBINED ATELOCOLLAGEN/POLYHOLOSIDE WALL COAGULATED BY A DIVALENT CATION AND METHOD FOR MANUFACTURING THESE MICROCAPSULES AND COSMETIC OR PHARMACEUTICAL OR FOOD COMPOSITIONS CONTAINING THEM

[75] Inventors: Roland Allard, St Genis Laval; Alain Huc, Ste Foy Les Lyon, both of France

[73] Assignee: Coletica, Lyon, France

[21] Appl. No.: 975,582

[22] PCT Filed: Aug. 2, 1991

[86] PCT No.: PCT/FR91/00640

§ 371 Date: Feb. 9, 1993

§ 102(e) Date: Feb. 9, 1993

[87] PCT Pub. No.: WO92/02254

PCT Pub. Date: Feb. 20, 1992

[30] Foreign Application Priority Data

Aug. 3, 1990 [FR] France .................................. 90 09997

[51] Int. Cl.⁶ .................................................. A61K 9/52
[52] U.S. Cl. ........................ 424/499; 424/401; 424/489; 428/402.2; 264/4.3
[58] Field of Search ................... 424/489, 490 C, 424/491 C, 493 C, 499; 427/213.31, 213.33, 213.3; 428/402.2, 2; 514/54, 55, 56, 59, 773, 777, 963; 264/4.3

[56] References Cited

U.S. PATENT DOCUMENTS

| | | | |
|---|---|---|---|
| 4,428,894 | 1/1984 | Bienvenu | 264/9 |
| 4,780,321 | 10/1988 | Levy et al. | 424/499 |
| 4,818,279 | 4/1989 | Chaleat et al. | 75/5 C |
| 5,011,692 | 4/1991 | Fujioka et al. | 424/426 |
| 5,169,631 | 12/1992 | Rase et al. | 424/401 |

FOREIGN PATENT DOCUMENTS

| | | |
|---|---|---|
| 1175618 | 10/1984 | Canada . |
| 0381543 | 8/1990 | European Pat. Off. . |
| 1388580 | 3/1975 | United Kingdom . |

*Primary Examiner*—Jyothsna Venkat
*Attorney, Agent, or Firm*—Lowe, Price, LeBlanc & Becker

[57] ABSTRACT

The invention relates to microcapsules having a combined atelocollagen/polyholoside coagulated wall as well as to a method for producing them. According to the invention, the microcapsules are characterized in that they include a combined atelocollagen/polyholoside wall coagulated by a coagulant, preferably a divalent cation. These microcapsules are preferably prepared by a method which includes laminar-flow extrusion dislocated by individual droplet vibrations falling into a coagulation bath. The presence of the atelocollagen renders the microcapsules biocompatible. They are particularly suitable for the production of cosmetic, pharmaceutical or food compositions.

29 Claims, 1 Drawing Sheet

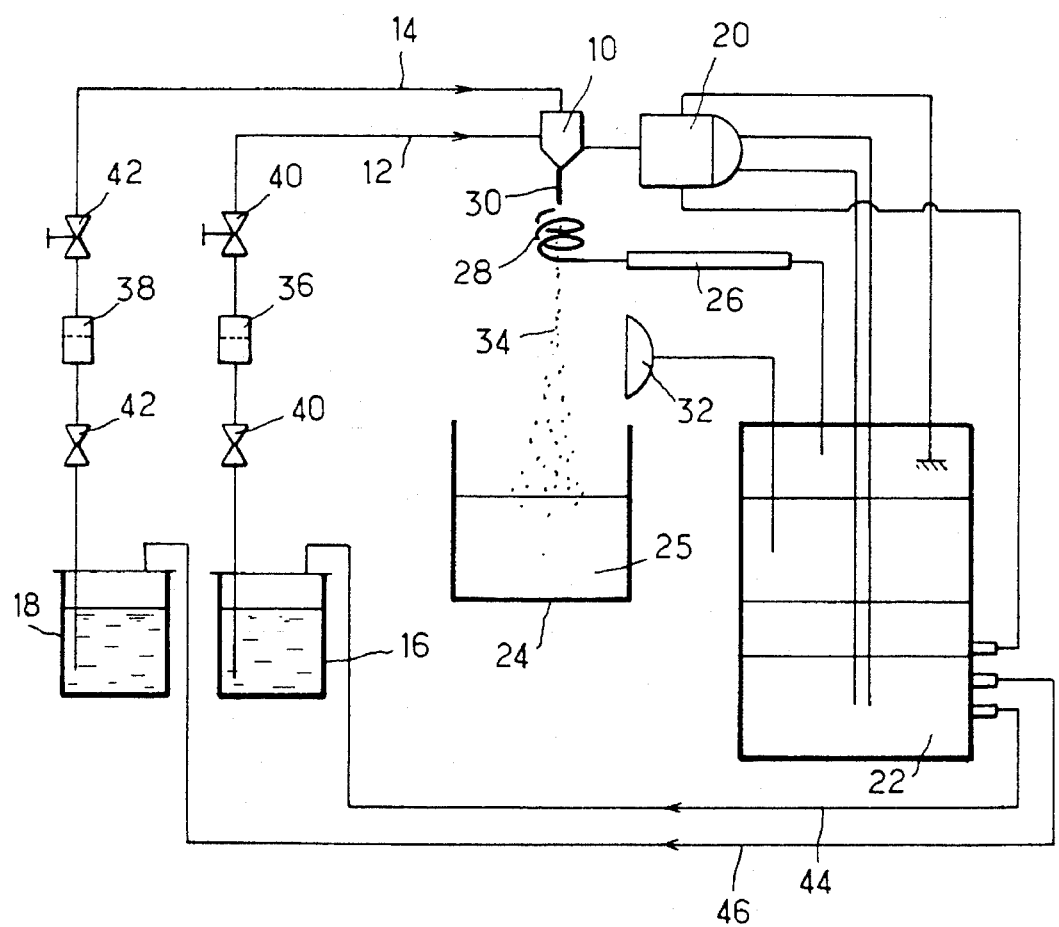

MICROCAPSULES HAVING A COMBINED ATELOCOLLAGEN/POLYHOLOSIDE WALL COAGULATED BY A DIVALENT CATION AND METHOD FOR MANUFACTURING THESE MICROCAPSULES AND COSMETIC OR PHARMACEUTICAL OR FOOD COMPOSITIONS CONTAINING THEM

The present invention essentially concerns microcapsules having a combined atelocollagen/polyholoside wall coagulated by a divalent cation, a method for manufacturing the microcapsules and cosmetic or pharmaceutical or food compositions containing them.

It is known that, for pharmaceutical and cosmetic applications, numerous research workers are working on the development of encapsulation of active substances. Among the effects sought for such work, particular mention may be made of the improvement in bio-availability, the protection of the active principle in a finished formula, the protection of the active principle in the organism in order to avoid in particular its degradation in the stomach, the deferred release or slow release for prolonged effect.

This encapsulation may be produced by incorporating these active principles in microcapsules for introduction thereof in cosmetic products, pharmaceutical preparations or food products intended for various routes of administration such as the oral route, parenteral route, application on the skin and the mucous membranes.

In the prior state of the art, various techniques have already been proposed for manufacturing microcapsules with the aid of synthetic polymers. These latter substances allow easy industrial manufacture but the microcapsules obtained are generally not easily biodegradable and, when they are, they produce products of degradation which may be toxic or whose toxicity is not known.

Thus, research work has been oriented towards the production of microcapsules with the aid of biocompatible or biodegradable natural substances. Within this scope, the research workers have used proteins. Reference may be made for example to document FR-A-2 444 497 MARS as well as to document FR-A-2 527 438 CNRS.

In both documents, the technique used comprises three steps:
a) the emulsifying of an alkaline aqueous solution of a protein within an organic solvent non-miscible in water;
b) the interface cross-linking of the vesicles of the emulsion thanks to a cross-linking agent which is generally an organic acid dichloride; and finally
c) the isolation and washing of the microcapsules obtained thanks to appropriate solvents.

In the first document, the membrane is constituted solely by protein, whilst, in the second document, it is composed of a mixture of proteins and polyholosides.

Another method known under the name of EXTRAMET process carried out by the firm EXTRAMET makes it possible to obtain microcapsules by mechanically cutting with the aid of a vibrator a laminar flow produced by extrusion of a solution of polymerizable materials through a nozzle, which provokes the formation of vesicles or droplets which may then be rigidified by drying or by cross-linking in a bath containing a cross-linking agent into which the vesicles or droplets drop. This technique may be applied to synthetic polymers or to proteins. The encapsulation of a hydrosoluble active substance in a protein capsule will be obtained by dissolution in the solution of proteins before extrusion. If the active substance is of oily form or if it is in solution in oil, it will be encapsulated thanks to a co-extrusion with the protein solution which lies outside the laminar flow.

It will be observed that, in neither of the documents of the prior state of the art relative to the manufacture of microcapsules and in particular in the two documents mentioned above, FR-A-2 444 497 and FR-A-2 527 438, although the methods are generally applied to proteins, has the use of collagen ever been mentioned or hinted at.

The inventors of the present invention have tried to use collagen in the methods described in the prior documents and by using the EXTRAMET technique.

These experiments resulted in failure as these techniques are not applicable to collagen. In fact, in order to obtain an efficient cross-linking, it is necessary to prepare solutions of collagen in a strongly buffered medium at pH's higher than or equal to 5.5.

Now, the usual collagen, i.e. native collagen, precipitates partly and it is then very difficult to obtain homogeneous mixtures. Emulsion with an organic liquid cannot be produced, with the result that the methods described in prior documents FR-A-2 444 497 and FR-A-2 527 438 cannot be employed. The same applies to the EXTRAMET laminar extrusion technique in which it is impossible to obtain a constant flux with a heterogeneous mixture.

Applicants have also described in document FR-A-2 642 329 the use of solutions of atelocollagen and of glycosaminoglycans for manufacturing the microcapsules by interface cross-linking with the aid of an interface cross-linking agent usually constituted by an acid chloride.

Unfortunately, this technique of interface cross-linking necessitates the use of diacid chloride for making capsules formed either by dispersion or by extrusion. The use of diacid chloride necessitates the use of an organic support agent. These two products must be completely eliminated by washing, which greatly weighs down the industrial method and largely limits the application thereof.

The present invention therefore has for an object to solve the new technical problem consisting in providing a solution for manufacturing microcapsules of which the wall comprises at least in part collagen or a product of collagen type presenting the same properties as collagen, in accordance with a simplified method of manufacture avoiding the use of cross-linking agent such as acid chlorides which must be eliminated.

The present invention also has for an object to solve the new technical problem set forth hereinabove, with the use of extremely simple methods of manufacture, usable on an industrial scale, and in addition making it possible to adjust as desired the dimensions of the microcapsules, in particular in a range of dimensions going from 100 to 3000 µm, in particular from 400 to 3000 µm.

According to the present invention, it has been totally unexpectedly discovered that the technical problems set forth hereinabove could be solved in extremely easy manner if a solution of atelocollagen and of polyholosides, for example glycosaminoglycans, which are coagulated with the aid of a divalent cation, for example calcium, magnesium, were used as raw material.

In this way, microcapsules are obtained, having noteworthy physico-mechanical properties, without having to carry out washing procedures contrarily to the prior known methods.

BRIEF DESCRIPTION OF THE DRAWINGS

FIG. 1 shows an Extramet apparatus used to make the microcapsules of the invention. This apparatus essentially comprises an extrusion nozzle 10 for effecting a co-extrusion by the presence of two concentric orifices supplied separately via two supply conduits 12, 14 serving for example respectively for the outer supply of atelocollagen-glycosaminoglycan solution according to the invention from a reservoir 16, and, inside, an active principle for example borage oil from an active principle reservoir 18. With this nozzle 10 is associated a vibrator device 20 controlled by control means 22. This apparatus includes a cross-linking bath 24 disposed at a distance beneath the nozzle 10 in which the solution of coagulating agent 25 is disposed. The apparatus includes an electrode 26 with helicoidal end 28 disposed concentrically to the flow of the laminar flux 30 co-extruded from the nozzle 10 so as to separate the droplets generated by the vibrator 20. A flash stroboscope device 32 may also be provided for visually observing the droplets thus generated dropping into the coagulation bath 25.

The droplets 34 generated by the vibrator 20 from the laminar flow made in the co-extrusion nozzle 10 are received in 1 l of coagulation bath 24 whose stirring is maintained. The bath is renewed after extrusion of 1 kg of the homogeneous atelocollagen-glycosaminoglycan solution.

Thus, according to a first aspect, the present invention has for an object microcapsules, characterized in that they comprise a combined wall of atelocollagen and polyholosides, for example glycosaminoglycans, coagulated by a coagulation agent preferably based on a divalent cation.

The proportion of polyholosides, for example glycosaminoglycans, with respect to atelocollagen may vary from 15 to 50% by weight.

According to a particular variant embodiment, the polyholosides are selected from the group consisting of glycosaminoglycans, such as structural glycosaminoglycans selected from the group consisting of chondroitine-4-sulfate, chondroitine-6-sulfate, dermatan-sulfate, heparane-sulfate, keratane-sulfate; as well as heparin and its derivatives; or dextran.

According to a particular variant embodiment, the combined wall is formed by coagulation of an atelocollagen-polyholoside mixture, in particular glycosaminoglycans or dextran, by introducing the solution of polyholosides in the solution of atelocollagen. In particular, the concentration of polyholosides in the solution of polyholosides is from 0.5 to 4% by weight, even better from 0.5 to 2%, and is preferably close to 1%.

According to another particular characteristic of the invention, the initial atelocollagen solution is an aqueous solution of atelocollagen having a concentration included between 0.5 and 2% by weight. This atelocollagen solution may be obtained according to the invention by dissolution of atelocollagen fibers in a slightly acid aqueous solution. These atelocollagen fibers are for example dissolved in 0.1M acetic acid. According to a variant embodiment, the atelocollagen may be obtained by enzymatic digestion of collagen.

According to another variant embodiment, there may be introduced into the initial aqueous solution of atelocollagen and glycosaminoglycans, or within the microcapsules, one or more desired active principles in the state of solution, suspension or emulsion, in particular one or more substances of cosmetic, pharmaceutical or food interest.

According to another particular embodiment of the invention, the divalent cation mentioned above used for coagulating the atelocollagen-polyholoside solution is a divalent cation selected from the group consisting of calcium, magnesium, manganese, barium, zinc, in particular in the form of a salt such as chloride or sulfate. Preferred salts are chloride salts. The coagulating agent is preferably present in a coagulation bath at a concentration ranging between 0.1 and 1% by weight. The higher this concentration, the harder the capsules obtained will be and the greater their mechanical strength.

These microcapsules may also include a third substance able to be coagulated by a coagulating agent, preferably a divalent cation, in particular a sodium alginate or casein.

An initial homogeneous composition of atelocollagen and of polyholosides will in that case comprise the following constituents intended to form the wall of the microcapsules:

atelocollagen 1 to 1.5% by weight polyholosides 0.3 to 0.5% by weight coagulatable substance 0.2 to 0.4% by weight The present invention also concerns a method for manufacturing microcapsules, characterized in that it comprises the following successive steps of:

a) preparing a solution of atelocollagen and a solution of polyholosides, separately;

b) mixing the solution of atelocollagen with the solution of polyholosides so as to form a homogeneous solution of atelocollagen and of polyholosides;

c) preparing a coagulation bath containing a coagulation agent, preferably a divalent cation;

d) forming individual droplets from the homogeneous solution of atelocollagen and of polyholosides which are made to drop into said coagulation bath, thus obtaining microcapsules by coagulation of the atelocollagen and the polyholosides under the effect of the coagulation agent; and e) separating the microcapsules by any appropriate means, particularly by natural decantation after having possibly effected one or more washings.

According to an advantageous characteristic of the method according to the invention, the coagulating agent is a divalent cation preferably selected from the group consisting of calcium, magnesium, manganese, barium, zinc, in particular in the form of salt such as a salt of chloride or sulfate, the chloride salt being preferred. The concentration of the divalent cation in the coagulation bath is advantageously included between 0.1 and 1% by weight.

According to a particular embodiment of the invention, there is also mixed in the atelocollagen-polyholoside solution a substance able to be coagulated by the coagulation agent, in particular a sodium alginate or casein.

According to another particularly advantageous embodiment of the method according to the invention, the individual droplets mentioned above are formed by a laminar extrusion of the homogeneous atelocollagen-polyholoside solution through an extrusion nozzle whilst subjecting the laminar flow to vibrations in order to dislocate the laminar flow into said individual droplets.

Furthermore, according to another variant embodiment enabling an active principle to be encapsulated, a laminar co-extrusion of the homogeneous atelocollagen-polyholoside solution and of the substance to be encapsulated is effected through an extrusion nozzle, whilst subjecting the laminar flow to vibrations in order to dislocate the laminar flow into individual droplets.

According to another variant embodiment of the methods according to the invention, the atelocollagen-polyholoside mixture is effected by introducing the solution of polyholosides into the solution of atelocollagen.

According to a particular embodiment, the solution of polyholosides is prepared by dissolution of the polyholoside, preferably obtained in the dry state, for example having been lyophilized, in an aqueous solution whose pH is adjusted so that, after mixture with the atelocollagen solution, the pH of the mixture is ranging between 5.5 and 10. The aqueous solution is preferably a basic buffer solution. This basic buffer solution may be an aqueous solution of sodium hydroxide or preferably an aqueous solution of a basic buffer obtained by neutralization of a weak acid with a strong base, such as for example sodium carbonate, sodium acetate or sodium citrate, or in solutions of phosphates of sodium and of potassium.

According to another advantageous characteristic of the methods according to the invention, the concentration of polyholosides with respect to the concentration of atelocollagen is from 15 to 50% by weight.

According to another advantageous characteristic of the methods according to the invention, the concentration of polyholosides in the polyholoside solution is from 0.5 to 4%, even better from 0.5 to 2%, and is preferably close to 1%.

According to another characteristic of the methods of the invention, the atelocollagen solution is an aqueous solution of atelocollagen having a concentration included between 0.5 and 2% by weight. This atelocollagen solution may be obtained according to the invention by dissolution of atelocollagen fibers in a slightly acid aqueous solution.

According to a particular embodiment, these atelocollagen fibers are dissolved in 0.1M acetic acid.

According to another particular embodiment of he methods according to the invention, the atelocollagen is obtained by enzymatic digestion of collagen.

According to a particular variant embodiment, the polyholosides used according to the invention are selected from the structural glycosaminoglycans selected from the group consisting of chondroitine-4-sulfate, chondroitine-6-sulfate, dermatane-sulfate, heparane-sulfate, keratane-sulfate; as well as heparin and its derivatives; or dextran.

There may be introduced into the aqueous atelocollagen-polyholoside solution one or more desired active principles in the state of solution, suspension or emulsion, in particular one or more substances of cosmetic, pharmaceutical or food interest.

In particular, in the extrusion technique mentioned above, an extrusion may be effected of the substance to be encapsulated incorporated within the laminar flow of atelocollagen and of polyholosides intended to constitute the wall of the microcapsules.

In the case of the oily phase being the encapsulated phase, it is possible to incorporate one or more substances of cosmetic, pharmaceutical or food interest in the state of solution, suspension or emulsion in this oily phase.

In particular, in the extrusion technique mentioned above, a co-extrusion may be effected of the active substance dissolved, in suspension or in emulsified form in the oily phase, within the laminar flow of atelocollagen and of polyholosides intended to constitute the wall of the microcapsules.

Finally, according to a third aspect, the present invention also concerns a cosmetic composition or a pharmaceutical composition, characterized in that it comprises microcapsules having combined atelocollagen-polyholoside wall coagulated by a coagulating agent, preferably a divalent cation. Preferably, these microcapsules contain at least in part one active principle, in particular a cosmetic active principle, a pharmaceutical active principle, or food.

Other objects, characteristics and advantages of the invention will clearly appear in the light of the following explanatory description given with reference to several embodiments of the invention given simply by way of illustration and which may therefore in no way limit the scope of the invention. In the examples, all the percentages are given by weight, unless indicated to the contrary.

BRIEF DESCRIPTION OF THE DRAWINGS

The enclosed single Figure schematically represents an apparatus for manufacturing microcapsules in accordance with the technique of extrusion of a laminar flow of the EXTRAMET type.

EXAMPLE 1 according to the invention

In this Example, microcapsules are manufactured, having a mean diameter of 600 μm containing oil of borage.

a) Preparation of decross-linked collagen or atelocollagen

The skin of a freshly slaughtered calf is subjected to chemical epilation in a bath containing 3% of sodium sulfide and 4% of lime, the proportion being 100 g of skin for 200 cm$^3$ of solution. The dermis is then isolated from the rest of the skin by a splitting using a rotating band saw.

The tissue obtained is ground and extruded through a grate comprising holes of 4 mm. The ground matter is then placed in contact for 3 weeks with a saturated milk of lime at a rate of 1 kg for 4 l of solution. The skin thus treated is separated from the supernatant matter by a continuous centrifugation with an acceleration of 2000 g with the aid of a decanter rotating at 4000 rpm. The remainder is then subjected to two washings in running water in a stainless steel vat with slow stirring at a rate of 1 kg for 4 l of bath. The ground matter is then subjected to two phosphate buffer treatments, pH 7.8 (21.7 g/l of $Na_2HPO_4$ and 0.78 g/l of $KH_2PO_4$) under the same conditions as for washing with water. The remainder is then washed in two baths of de-ionized and sterile water. The ground matter obtained is placed in a solution of acetic acid (0.5 g/l, pH 3.4) at a rate of 1 kg for 20 l of bath. After 5 minutes' stirring, the supernatant matter is separated from the remainder by continuous decantation in accordance with the preceding technique. The collagen is then precipitated by the supernatant matter by addition of dry sodium chloride in a proportion of about 10% with respect to the bath. After decantation by gravity, the fibers obtained are dialyzed against de-ionized and sterile water with the aid of dialysis membranes, preferably formed by tubing of which the cutting threshold is ranging between 6000 and 8000 daltons.

b) Preparation of the chondroitine-4-sulfate

Lambs' septa nasi from which the muscular and adipose tissues have been removed are chopped and ground by extrusion through a grate comprising holes of 4 mm; the ground matter is placed for 24 hours at a temperature of 6° C. in a potassium chloride buffer (11.8 g/l of KCl, 78.8 mg/l of cysteine, ETDA 180 mg/l) containing 1% of "MERCK" papain. The proportion being 130 g of ground matter for 1 l of buffer.

The supernatant matter is separated from the remainder by continuous centrifugation with the aid of a decanter rotating at 4000 rpm. To the supernatant matter are then added 40 g/l of trichloroacetic acid. The precipitate is eliminated by continuous centrifugation in accordance with the preceding technique. The supernatant matter is neutralized with the aid of sodium hydroxide in pellet form. The mixture is then dialyzed against de-ionized and sterile water with the aid of tubing of which the cutting threshold is ranging between 6000 and 8000 daltons. The dialyzed solution is lyophilized. The chondroitine-4-sulfate is obtained in the dry state.

c) Preparation of the homogeneous solution of atelocollagen and chondroitine-4-sulfate in a buffered medium at pH 7.5

The atelocollagen in fiber form coming from the dialysis tubing is dissolved in an aqueous 0.1M acetic acid solution so as to obtain an atelocollagen concentration of 3.2%.

This solution is diluted by a solution of chondroitine-4-sulfate in sodium hydroxide whose volume and concentrations are such that the final concentrations of the homogeneous mixture of atelocollagen and chondroitine-4-sulfate are those given in the table hereinafter and that the pH of the medium is close to 7.5:

atelocollagen 1.5% chondroitine-4-sulfate 0.5% sodium alginate 0.3%

Nipagin® 0.4% from Nipa Laboratories Ltd. (UK).

de-ionized water balance

The pH of the solution is adjusted to 7.5 either by sodium hydroxide or by hydrochloric acid. 2 kg of this solution is thus prepared.

d) Preparation of the coagulating agent 55.5 g of calcium chloride as well as 10 g of ethyl alcohol are dissolved in 5 l of de-ionized water. On the surface is deposited a layer, 1 to 2 cm thick, of a fatty acid ester available on the market, for example known under the commercial name DRAGOXAT® sold by the firm DRAGOCO. A second, identical bath is also prepared.

e) Co-extrusion and coagulation of the capsules

To that end, the Extramet apparatus shown schematically in the accompanying single Figure is used.

This apparatus essentially comprises an extrusion nozzle 10 for effecting a co-extrusion by the presence of two concentric orifices supplied separately via two supply conduits 12, 14 serving for example respectively for the outer supply of atelocollagen-glycosaminoglycan solution according to the invention from a reservoir 16, and, inside, an active principle for example borage oil from an active principle reservoir 18. With this nozzle 10 is associated a vibrator device 20 controlled by control means 22. This apparatus also comprises a cross-linking bath 24 disposed at a distance beneath the nozzle 10 in which the solution of coagulating agent 25 is disposed.

This apparatus also comprises an electrode 26 with helicoidal end 28 disposed concentrically to the flow of the laminar flux 30 co-extruded from the nozzle 10 so as to separate the droplets generated by the vibrator 20. A flash stroboscope device 32 may also be provided for visually observing the droplets thus generated dropping into the coagulation bath 25.

The flowrate of the homogeneous atelocollagen-glycosaminoglycan solution present in the tank 16 is 2.4 l/hr and that of the borage oil present in tank 18, constituting the active principle, is 1.2 l/hr. The frequency of vibration of the vibrator 20 is 230 Mhz. The diameters of the two concentric orifices are 400 and 600 μm.

The droplets 34 generated by the vibrator 20 from the laminar flow made in the co-extrusion nozzle 10 are received in 1 l of coagulation bath 24 whose stirring is maintained. The bath is renewed after extrusion of 1 kg of the homogeneous atelocollagen-glycosaminoglycan solution.

f) Washing and storage

The capsules recovered by filtration are placed in a bath of 10 l of de-ionized water and maintained with stirring for 15 mins. At the end of this period of time, they are again recovered by filtration and placed in a bath of 2 l of de-ionized water in which was previously dissolved 1% of a solution of phenonip® from Nipa Laboratories Ltd. (UK) in propyleneglycol. The volumes of these two latter compounds being equal. Under such conditions, the capsules may be stored at ambient temperature.

EXAMPLE 2 according to the invention

Manufacture of microcapsules of mean diameter 400 μm containing an extract of Ginko Biloba (firm Alban Müller).

a) Preparation of the homogeneous solution of atelocollagen and of chondroitine-4-sulfate in a buffered medium at pH 9.8

1 kg of this homogeneous solution is prepared as described in Example 1. In this solution are dissolved 7% of extract of Ginko Biloba and the pH is again adjusted to 7.5.

b) Extrusion and coagulation of the microcapsules

Extrusion and coagulation of the microcapsules are carried out under the same conditions as those described in Example 1, except concerning the flowrate which is 2 l/hr for the homogeneous solution of atelocollagen and of chondroitine-4-sulfate containing the extract of Ginko Biloba.

c) Washing and storage of the microcapsules

The capsules are received in a coagulation bath of 5 l identical to that described in Example 1. They are washed and stored under the same conditions.

For use in pharmaceutical compositions, these microcapsules make it possible, when used by the oral route, to mask the taste of the active principle, and afford protection in the stomach or produce a deferred effect thanks to a gastro-resistance which may be obtained by an appropriate coagulation.

Compositions intended for various routes of administration, such as the oral route, the parenteral route, application on the skin and the mucous membranes, may also be produced.

The present invention also generally concerns a method for preparing a cosmetic, pharmaceutical or food composition, characterized in that microcapsules having combined coagulated atelocollagen-polyholoside wall, are incorporated at least in part, in which a substance presenting a cosmetic, pharmaceutical or food interest has preferably been encapsulated at least in part.

These microcapsules also allow the protection of fragile substances such as essential oils which may be included in the composition of the food.

Other uses of these microcapsules will clearly appear to the man skilled in the art.

We claim:

1. Microcapsules comprising a combined wall of atelocollagen and polyholoside coagulated by a coagulation agent comprising a divalent cation.

2. Microcapsules according to claim 1 wherein the divalent cation is selected from the group consisting of calcium, magnesium, manganese, barium, and zinc.

3. Microcapsules according to claim 1, wherein the proportion of polyholoside with respect to the atelocollagen ranges from 15 to 50% by weight.

4. Microcapsules according to claim 1, wherein the polyholoside is a glycosaminoglycan.

5. Microcapsules according to claim 1, wherein the wall further comprises a coagulatable substance able to be coagulated by the coagulation agent.

6. Microcapsules according to claim 1 further comprising an active substance selected from the group consisting of Gingko biloba and borage oil as part of the microcapsule.

7. Microcapsules according to claim 5, wherein the constituents of the initial composition which form the wall of the microcapsules are the following:

atelocollagen 1 to 1.5% by weight polyholosides 0.3 to 0.5% by weight coagulatable substance 0.2 to 0.4% by weight.

8. Method for manufacturing microcapsules comprising the following successive steps:

a) preparing a solution of atelocollagen and a solution of polyholosides separately;

b) mixing the solution of atelocollagen with the solution of polyholosides, so as to form a homogeneous solution of atelocollagen and of polyholosides;

c) preparing a coagulation bath containing a coagulation agent comprising a divalent cation;

d) forming individual droplets from the homogeneous solutions which are made to drop into said coagulation bath, thus obtaining microcapsules by coagulation of the atelocollagen and of the polyholosides under the effect of the coagulation agent; and e) separating the microcapsules from the coagulation bath.

9. Method according to claim 8, wherein the individual droplets are formed by laminar extrusion of the homogeneous solution through an extrusion nozzle while subjecting the laminar flow to vibrations, thereby dislocating the laminar flow into individual droplets.

10. Method according to claim 8, wherein individual droplets encapsulating an active substance selected from the group consisting of Ginko biloba and Borage oil are formed by effecting through an extrusion nozzle a laminar co-extrusion of the homogeneous solution of atelocollagen and of polyholoside and of the encapsulated substance, while subjecting the laminar flow to vibrations to dislocate the laminar flow into said individual droplets encapsulating said active substance.

11. Method according to claim 8, wherein the atelocollagen-polyholosides mixture is made by introducing the solution of polyholosides into the solution of atelocollagen.

12. Method according to claim 8, wherein the polyholoside solution is prepared by placing the polyholoside in an aqueous solution and the pH is adjusted so that, after mixing with the atelocollagen solution, the pH of the mixture ranges between 5.5 and 10.

13. Method according to claim 12, wherein the aqueous solution is a basic buffer solution formed from a substance selected from the group consisting of sodium hydroxide, sodium carbonate, sodium acetate, sodium citrate, sodium phosphate and potassium phosphate.

14. Method according to claim 13, wherein the concentration of polyholoside with respect to the concentration of atelocollagen is from 15 to 50% by weight.

15. Method according to claim 10, wherein the concentration of polyholoside in the polyholoside solution is from 0.5 to 4% by weight.

16. Method according to claim 10, wherein the concentration of atelocollagen in the atelocollagen solution ranges between 0.5 and 2% by weight.

17. Method according to claim 16, wherein the atelocollagen solution is obtained by dissolution of atelocollagen fibers in a slightly acid aqueous solution.

18. Method according to claim 8, wherein the polyholoside is selected from the group consisting of chondroitine-4-sulfate, chondroitine-6-sulfate, dermatane-sulfate, heparane-sulfate, keratane-sulfate, heparin and dextran.

19. Method according to claim 8, wherein an active substance selected from the group consisting of Gingko biloba and borage oil is introduced into the aqueous solution of atelocollagen and polyholoside.

20. Method according to claim 8, wherein an active substance selected from the group consisting of Ginko biloba and Borage oil encapsulated in the microcapsules.

21. Method according to claim 19, wherein the active substance and the atelocollagen and polyholoside are extruded.

22. Method according to claim 19, wherein the active substance is co-extruded with the aqueous solution of atelocollagen and of polyholoside, said coextrusion being effected with an extrusion nozzle having two concentric orifices comprising an outer concentric orifice and an inner concentric orifice, said outer orifice being supplied with aqueous solution of atelocollagen and of polyholoside and said inner orifice being supplied with said active substance.

23. A pharmaceutical composition comprising microcapsules comprising a substance selected from the group consisting of Gingko biloba and borage oil with a atelocollagen-polyholoside coagulated wall in the form adapted for a route of administration selected from the group consisting of oral route, parenteral route, application on skin and application on mucous membranes.

24. Microcapsules according to claim 4, wherein the glycosaminoglycan is selected from the group consisting of chondroitine-4-sulfate, chondroitine-6-sulfate, dermatane-sulfate, heparin-sulfate and keratane-sulfate.

25. Microcapsules according to claim 5, wherein the substance to be coagulated by the coagulation agent is selected from the group consisting of an alginate salt and casein.

26. The method of claim 12, wherein the polyholoside solution is obtained by solving a polyholoside obtained in the dry state.

27. Method according to claim 13, wherein said basic buffer is prepared from the neutralization product of a weak acid with a strong base.

28. Method according to claim 15, wherein the concentration of polyholoside in the polyholoside solution is from 0.5 to 2% by weight.

29. Method according to claim 17, wherein said slightly acid aqueous solution is a 0.1M acetic acid aqueous solution.

* * * * *